(12) United States Patent
Park et al.

(10) Patent No.: US 11,969,285 B2
(45) Date of Patent: Apr. 30, 2024

(54) DOSE ADJUSTMENT DEVICE MOUNTABLE TO DIAGNOSTIC RADIATION EQUIPMENT AND DOSE ADJUSTMENT SYSTEM INCLUDING SAME

(71) Applicant: KOREA INSTITUTE OF RADIOLOGICAL & MEDICAL SCIENCES, Seoul (KR)

(72) Inventors: Seung Woo Park, Seoul (KR); Jong Hyun Back, Changwon (KR)

(73) Assignee: KOREA INSTITUTE OF RADIOLOGICAL & MEDICAL SCIENCES, Seoul (KR)

( * ) Notice: Subject to any disclaimer, the term of this patent is extended or adjusted under 35 U.S.C. 154(b) by 282 days.

(21) Appl. No.: 17/636,778

(22) PCT Filed: Jun. 17, 2020

(86) PCT No.: PCT/KR2020/007800
§ 371 (c)(1),
(2) Date: Feb. 18, 2022

(87) PCT Pub. No.: WO2021/033900
PCT Pub. Date: Feb. 25, 2021

(65) Prior Publication Data
US 2022/0296198 A1    Sep. 22, 2022

(30) Foreign Application Priority Data
Aug. 20, 2019 (KR) .................. 10-2019-0101964

(51) Int. Cl.
*A61B 6/06* (2006.01)
*A61B 6/00* (2006.01)
*A61B 6/46* (2024.01)

(52) U.S. Cl.
CPC ................. *A61B 6/542* (2013.01); *A61B 6/06* (2013.01); *A61B 6/463* (2013.01); *A61B 6/465* (2013.01); *A61B 6/467* (2013.01); *A61B 6/56* (2013.01)

(58) Field of Classification Search
CPC ........... A61B 6/542; A61B 6/06; A61B 6/463; A61B 6/465; A61B 6/467; A61B 6/56
See application file for complete search history.

(56) References Cited

U.S. PATENT DOCUMENTS 5,680,434 A      10/1997   Thelosen et al.
10,398,911 B2 *  9/2019    Nord .................. G21K 1/046
(Continued)

FOREIGN PATENT DOCUMENTS

JP    2003-225235 A    8/2003
JP    2004073405 A     3/2004
(Continued)

OTHER PUBLICATIONS

The Extended European Search Report for European Patent Application No. 20854895.8, dated Jul. 20, 2023.

*Primary Examiner* — David P Porta
*Assistant Examiner* — Fani Polyzos Boosalis

(57) ABSTRACT

The present invention relates to the dose adjustment device mountable to diagnostic radiation equipment and the dose adjustment system which allows radiation exposure in each portion of in the irradiation area to be prevented, and are configured as modules that are attachable to diagnostic radiation equipment, thus having the effect of allowing a radiation shielding function to be easily added to existing equipment without changing the structure thereof.

14 Claims, 15 Drawing Sheets

(56) References Cited

U.S. PATENT DOCUMENTS

| | | | |
|---|---|---|---|
| 10,500,417 B2* | 12/2019 | Kuusela | A61N 5/1045 |
| 11,000,706 B2* | 5/2021 | Kawrykow | A61N 5/1049 |
| 2003/0202632 A1 | 10/2003 | Svatos | |
| 2004/0247016 A1* | 12/2004 | Faries, Jr. | A61M 5/445 |
| | | | 374/E11.018 |
| 2008/0118023 A1 | 5/2008 | Besson | |
| 2017/0151444 A1 | 6/2017 | Li et al. | |
| 2018/0161602 A1 | 6/2018 | Kawrykow | |

FOREIGN PATENT DOCUMENTS

| | | |
|---|---|---|
| JP | 2017-502274 A | 1/2017 |
| KR | 20130104965 A | 9/2013 |
| KR | 20160090060 A | 7/2016 |
| KR | 101674529 B1 | 11/2016 |
| KR | 20170055806 A | 5/2017 |
| KR | 20190092530 A | 8/2019 |
| WO | 2018/147541 A1 | 8/2018 |

* cited by examiner

DOSE ADJUSTMENT DEVICE MOUNTABLE TO DIAGNOSTIC RADIATION EQUIPMENT AND DOSE ADJUSTMENT SYSTEM INCLUDING SAME

TECHNICAL FIELD

The disclosure relates to a dose adjustment device mountable to a diagnostic radiation apparatus and a dose adjustment system including the same, and more particularly to a dose adjustment device, which is mounted to a diagnostic radiation apparatus and capable of adjusting the dose of radiation for each portion in an irradiation area, and a dose adjustment system including the same.

BACKGROUND ART

A diagnostic radiation apparatus refers to an apparatus that noninvasively obtains information about the interior of a body at radioscopic angiography and radiologic intervention. The diagnostic radiation apparatus continuously emits radiation for a predetermined period of time to obtain information about the interior of a body in real time, and therefore involves exposure to a considerable amount of radiation in spite of using low-energy radiation.

Conventionally, to reduce the amount of radiation to which a patient is exposed while the diagnostic radiation apparatus is in use, a range of the exposure to the radiation has been limited in such a manner that a shielding material is directly attached to the patient's body or the patient wears protective clothing. Further, the range of the exposure to the radiation has been limited in such a manner that a radiation irradiator employs a collimator, by which area setting is restrictively possible, while maintaining a fixed field shape. Regarding such dose reduction technology of the diagnostic radiation apparatus, there is U.S. Pat. No. 5,680,434 (registered on Oct. 21, 1997).

However, such a conventional diagnostic radiation apparatus has a limitation on reducing the exposure to the radiation in areas unrelated to diagnosis because the range of the exposure is set in a typical shape.

DISCLOSURE

Technical Problem

An aspect of the disclosure is to solve the foregoing limitation of a conventional diagnostic radiation apparatus and aims to provide a dose adjustment device mountable to a diagnostic radiation apparatus, which can adjust shielding for each portion, and a dose adjustment system including the same.

Technical Solution

According to the aspect of the disclosure, there may be provided a dose adjustment device mountable to a diagnostic radiation apparatus including: a power supply; a multi-leaf collimator configured to adjust transmittance for a portion in an irradiation area of diagnostic radiation; an actuator configured to individually adjust positions of single-leaves included in the multi-leaf collimator; a communication module configured to communicate with an outside; and a controller configured to control the actuator so that the transmittance for each portion in the irradiation area of the diagnostic radiation can be adjusted based on a signal received from the communication module.

Here, the dose adjustment device may be provided between a radiation irradiator and a radiation detector of the diagnostic radiation apparatus.

Further, the dose adjustment device may further include a connector detachably provided at an end portion of the radiation irradiator of the diagnostic radiation apparatus.

Meanwhile, the single-leaves may each extend on a plane perpendicular to an irradiating direction of the radiation, and be provided side by side being in close contact with each other.

Meanwhile, the actuator may include a plurality of actuation units to move each single-leaf in a direction where the single-leaf extends.

Meanwhile, the dose adjustment device may further include a cylindrical housing accommodating the power supply, the multi-leaf collimator, the communication module, and the controller, and formed with a hole in a center portion thereof through which the diagnostic radiation can pass.

Furthermore, the multi-leaf collimator may be configured in two rows on the plane, and each row may be configured to adjust the transmittance of a half area in the hole.

The collimator module, the power supply, the communication module and the controller may be stacked as a plurality of layers inside the housing.

Meanwhile, the radiation may include an X-ray.

Meanwhile, the single-leaf may be configured to shield the X-ray.

Further, the single-leaf may be configured to transmit 1% to 99% of the X-ray.

In addition, there may be provided a dose adjustment system mountable to a diagnostic radiation apparatus, including: a dose adjustment device detachably provided in the diagnostic radiation apparatus; and a control device configured to communicate with the dose adjustment device and receive an input of an adjustment amount for transmittance of radiation for a portion, the dose adjustment device including: a power supply; a multi-leaf collimator configured to adjust transmittance for a portion in an irradiation area of diagnostic radiation; an actuator configured to individually adjust positions of single-leaves included in the multi-leaf collimator; a communication module configured to communicate with the control device; and a controller configured to control the actuator so that the transmittance for each portion in the irradiation area of the diagnostic radiation can be adjusted based on a signal received from the communication module.

Here, the control device may include a display, and is configured to receive an obtained diagnostic image from an external diagnostic radiation apparatus and display the received diagnostic image on the display.

Further, the control device may be configured to generate an adjustment signal for adjusting the multi-leaf collimator based on a touched position and a dragged amount when a user touches and drags an image on the display, and the controller may control the actuator based on the adjustment signal.

Advantageous Effects

A dose adjustment device mountable to a diagnostic radiation apparatus according to the disclosure and a dose adjustment system including the same have effects on preventing exposure to radiation for each portion in a radiation irradiation area, and easily adding a radiation shielding function to the existing equipment without structural changes because the dose adjustment device is modularized to be mountable to the diagnostic radiation apparatus.

MODE FOR INVENTION

Figure 1:
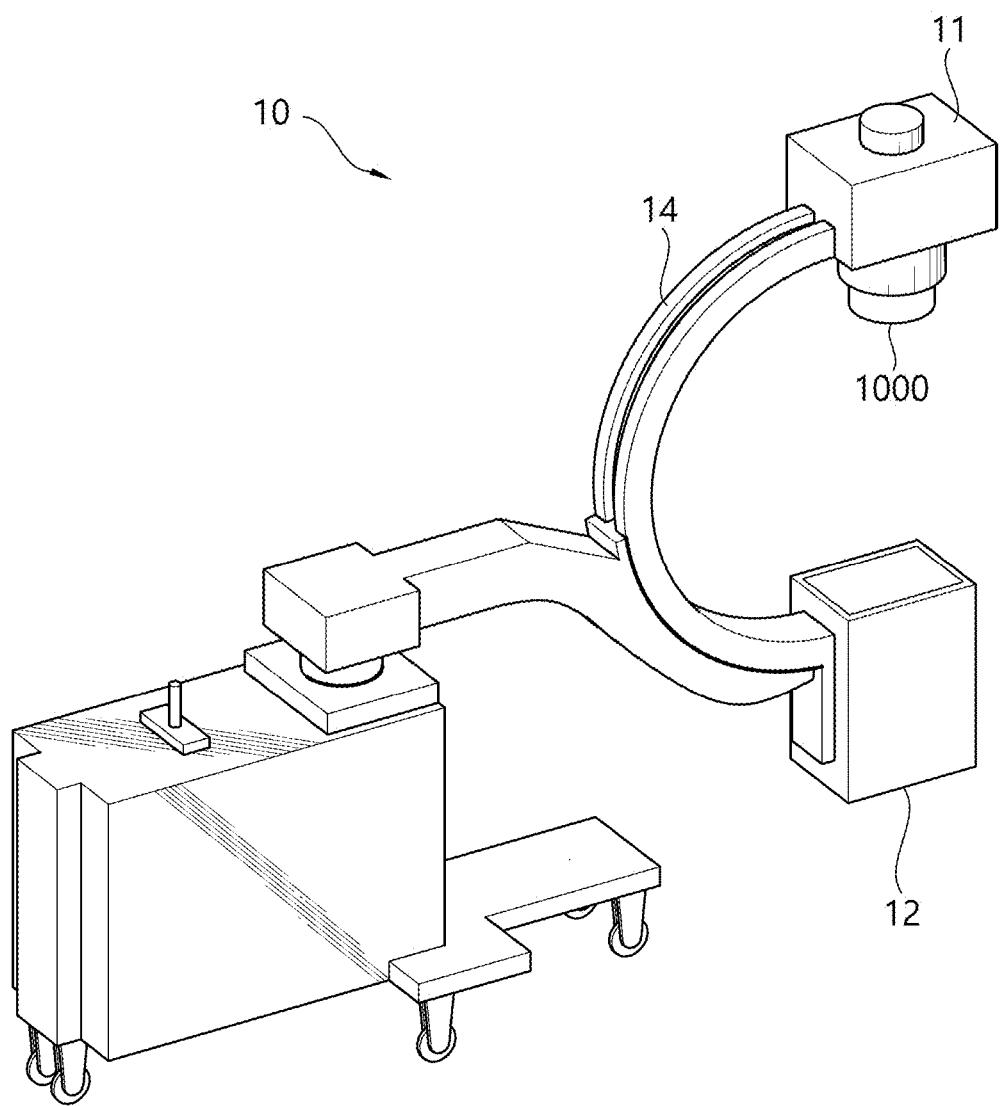
FIG. 1 is a perspective view of a mobile diagnostic radiation apparatus with a dose adjustment device according to the disclosure.

Hereinafter, a dose adjustment device mountable to the diagnostic radiation apparatus and a dose adjustment system including the same according to embodiments of the disclosure will be described in detail with reference to the accompanying drawings. Elements described in embodiments set forth herein may be called other names in the art. However, if the elements are similar or identical in terms of their functions, they may be regarded as equivalents even in alternative embodiments. Further, symbols assigned to the elements are given for convenience of description. However, content on the drawings with these given signs do not limit the elements to a range in the drawings. Likewise, even though the elements on the drawings are partially modified according to alternative embodiments, they having functional similarity and identity may be regarded as equivalents. Further, if those skilled in the art recognizes natural involvement of elements, descriptions of the elements will be omitted.

Below, a multi-leaf collimator module according to the disclosure will be described in detail with reference to FIGS. 1 to 5B.

FIG. 1 is a perspective view of a mobile diagnostic radiation apparatus with a dose adjustment device according to the disclosure.

As shown therein, the dose adjustment device according to the disclosure is provided as an add-on to the diagnostic radiation apparatus, and configured to add a function of adjusting the amount of radiation shielding for each portion in a radiation irradiation area.

Meanwhile, the diagnostic radiation apparatus, to which the disclosure is applied, may be distinguished from a therapeutic radiation apparatus. The therapeutic radiation apparatus uses high-energy radiation, and thus its essential elements such as an accelerating tube, a collimator, a collimator actuator, a power supply, etc. are installed and used on a large scale. On the other hand, the diagnostic radiation apparatus uses low-energy radiation, and is thus miniaturized and portable. Therefore, the collimator module according to the disclosure may be modularized as a compact and small element that can be actuated independently.

Figure 2:
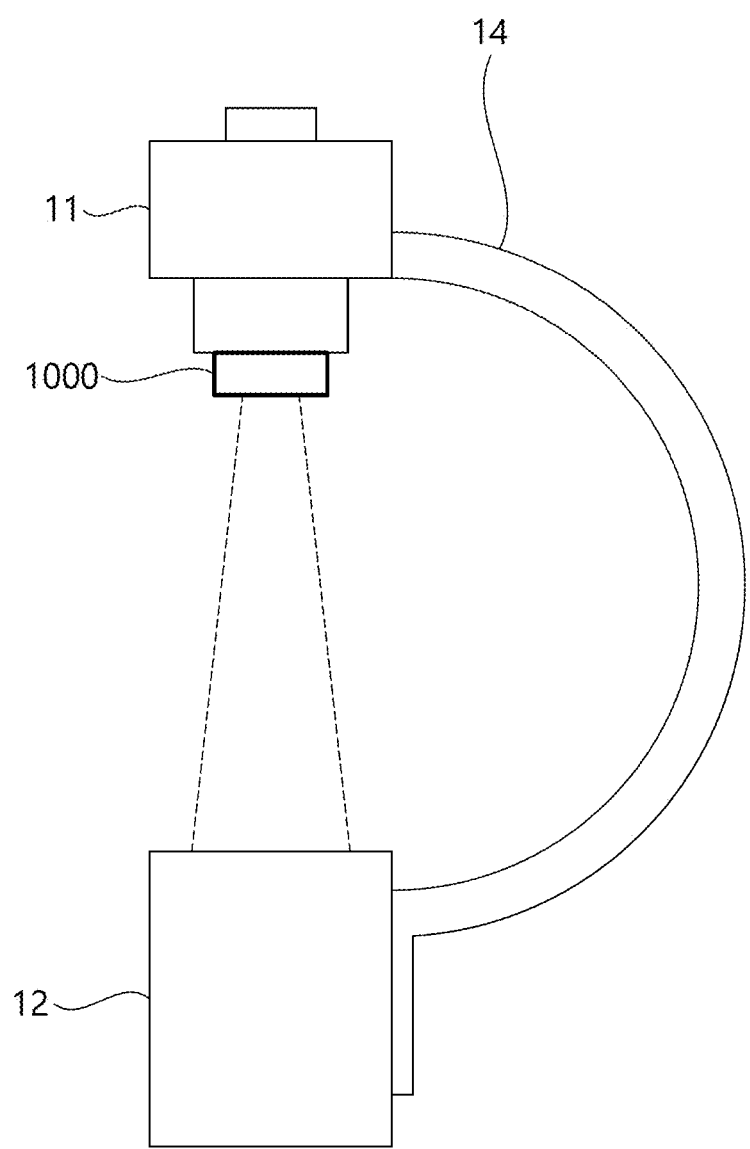
FIG. 2 is an enlarged view of C-arm parts in FIG. 1.

FIG. 2 is an enlarged view of C-arm parts in FIG. 1. The dose adjustment device according to the disclosure may be placed in a space between a radiation irradiator and a radiation detector of the diagnostic radiation apparatus. For example, as shown in FIG. 2, the dose adjustment device is provided at an end portion of the radiation irradiator, thereby easily adding a function of adjusting a radiation shielding rate for each portion without separate structural changes.

Figure 3:
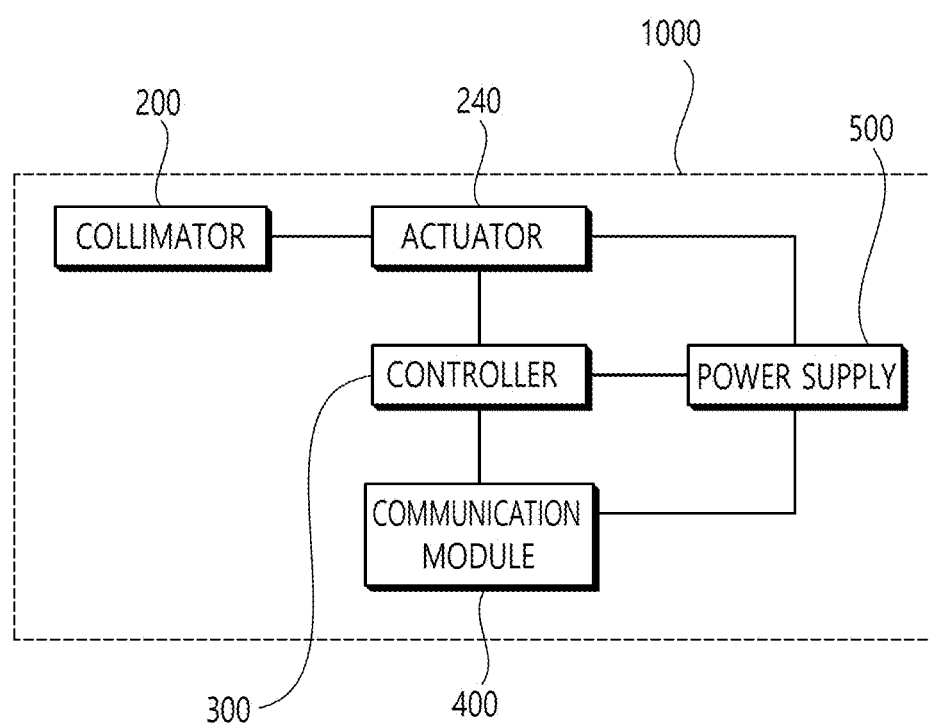
FIG. 3 is a block diagram of a dose adjustment device according to an embodiment of the disclosure.

FIG. 3 is a block diagram of a dose adjustment device according to an embodiment of the disclosure.

As shown therein, the dose adjustment device according to the disclosure may include a multi-leaf collimator module, a communication module, a power supply, and a controller.

The multi-leaf collimator module may include a multi-leaf collimator, and an actuator. The multi-leaf collimator includes a plurality of single-leaves, so that the plurality of single-leaves can be combined to adjust the amount of radiation shielding for each portion. The multi-leaf collimator may be provided side by side on a plane perpendicular to an irradiating direction of the radiation. Each single-leaf 220 may extend a predetermined length in its lengthwise direction, and be in close contact with other single-leaves 220 in its widthwise direction. The single-leaves 220 may be arranged to have bilateral symmetry. The left single-leaves 220 and the right single-leaves 220 are provided to respectively adjust the shielded areas at both sides while bisecting a plurality of divided radiation irradiation areas. The radiation shielding rate of the single-leaf 220 may be varied depending on the material and thickness of the single-leaf 220. According to the features of the single-leaf 220, an image of a shielded area may be selected to be opaque or translucent. Meanwhile, detailed operations of such a collimator will be described later.

A actuator 240 is configured to move the single-leaf 220 in the lengthwise direction. The actuator 240 may include actuation units 241 as many as the number of single-leaves 220 to move the single-leaves 220 independently of each other. Each actuation unit 241 is connected to one side of the single-leaf 220 and has an actuation amount based on a signal of a controller 300 (to be described later).

A communication module 400 is configured to communicate with an external device. The communication module 400 receives a signal, which is input by a user for the position of the collimator 300, and transmits the received signal to the collimator 300.

A power supply 500 may be configured to supply power to electric elements including the actuator 240, the communication module 400 and the controller 300. The power supply 500 may include a secondary battery so that charged energy can be used even when power is not separately supplied.

The controller 300 may be configured to control the communication module 400 and the actuator 240. When a user's input is received through the communication module 400, the controller 300 identifies an actuation amount based on the input and ultimately changes a position combination of the multi-leaf collimator.

Below, the structure and shape of a dose adjustment device 1000 according to the disclosure will be described in detail with reference to FIGS. 4 and 5B.

Figure 4:
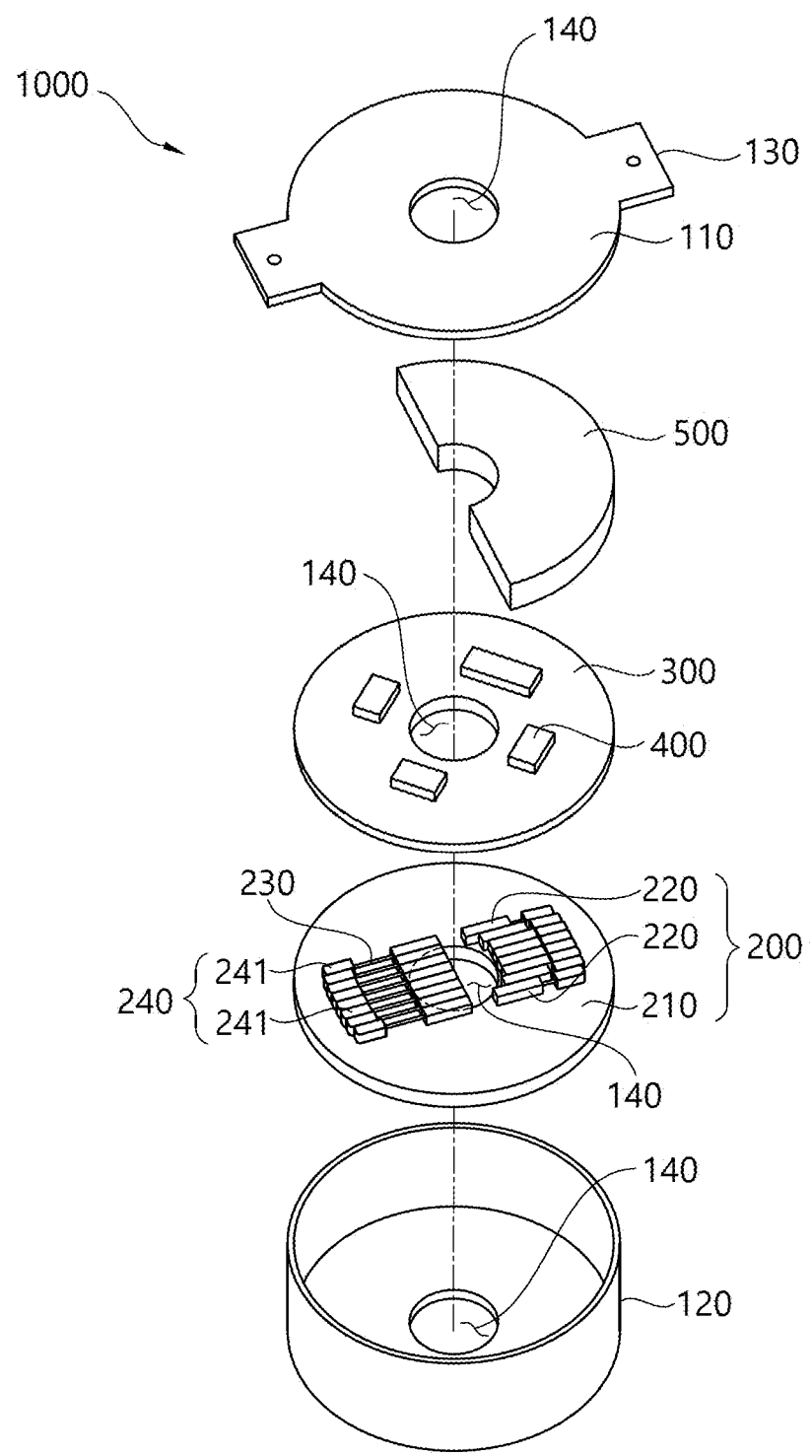
FIG. 4 is an exploded perspective view of a dose adjustment device according to the disclosure.

FIG. 4 is an exploded perspective view of the dose adjustment device 1000 according to the disclosure.

As shown therein, the dose adjustment device 1000 according to the disclosure may be provided as a single body and mounted to a diagnostic radiation apparatus 10. For example, the dose adjustment device 1000 may be shaped like a cylinder having a low height, and formed with a hole 140 in a center portion thereof to pass radiation therethrough.

The dose adjustment device 1000 may include a multi-leaf collimator module 200, a controller 300, the communication module 400, and the power supply 500, which are placed inside a housing 100.

The housing 100 may include an upper cap 110, a lower cap 120, and a connector 130. The upper cap 110 may be provided to include a top side of the housing 100, and the lower cap 120 may be provided to include a bottom side of the housing 100. The top and bottom sides are respectively formed with the holes 140 having a predetermined inner diameter to pass radiation therethrough. The upper cap 110 may be provided with the connectors 130 protruding at opposite sides so as to be easily connected to a radiation irradiator 11. The structure of the housing 100 is described by taking the shape shown in FIG. 4 as an example, but the housing may have various structures as long as it can place the multi-leaf collimator, the actuator 240 and the controller 300 therein. Further, the connector 130 may also have various structures for the connection with the end portion of the radiation irradiator 11.

The battery, the controller 300, and the multi-leaf collimator module 200 may be stacked inside the housing 100. It is possible to maintain the easiness of mounting the dose adjustment device 1000 to the end portion of the radiation irradiator 11 and the easiness of controlling the diagnostic radiation apparatus 10 after the mounting.

The battery may be shaped like a disk to enhance a spatial efficiency when being loaded into the housing 100. Specifically, the battery may be shaped to form a part of the disk so that a structure for connection with an external power source can be disposed on the same layer.

The controller 300 and the communication module 400 may be provided on a substrate. The substrate may also be shaped like a disk formed with the hole 140 in a center portion thereof to pass the radiation therethrough.

The multi-leaf collimator module 200 may include a base 210 shaped like a disk formed with the hollow 140 in a center portion thereof, and include the multi-leaf collimator, a shaft 230 and the actuator 240 which are disposed on the base 210. The base 210 may have a symmetric axis as a central axis bisecting the plane thereof, and the multi-leaf collimator and the actuator 240 may be arranged to have bilateral symmetry. The outer diameter of the base 210 may be set to allow the single-leaf 220 to reciprocate between a state where the hollow 140 is fully closed and a state where the hollow 140 is fully opened. The base 210 may include a linear guide (not shown) to guide the moving direction of the single-leaf 220 so that the single-leaf 220 can reciprocate along a given path.

The actuator 240 may include a plurality of actuation units 241 to respectively move the single-leaves 220 as described above. The plurality of actuation units 241 may be arranged in parallel with the lengthwise direction of the single-leaves 220, and disposed outward on the plane of the base 210. The shaft 230 may be provided in plural to connect each actuation unit 241 and one side of each single-leaf 220. However, this structure of the shaft 230 is merely an example, and the shaft 230 may have various connection structures as long as the actuation unit 241 can move the single-leaf 220.

Below, the operations of the multi-leaf collimator module 200 will be described in detail.

Figure 5A:
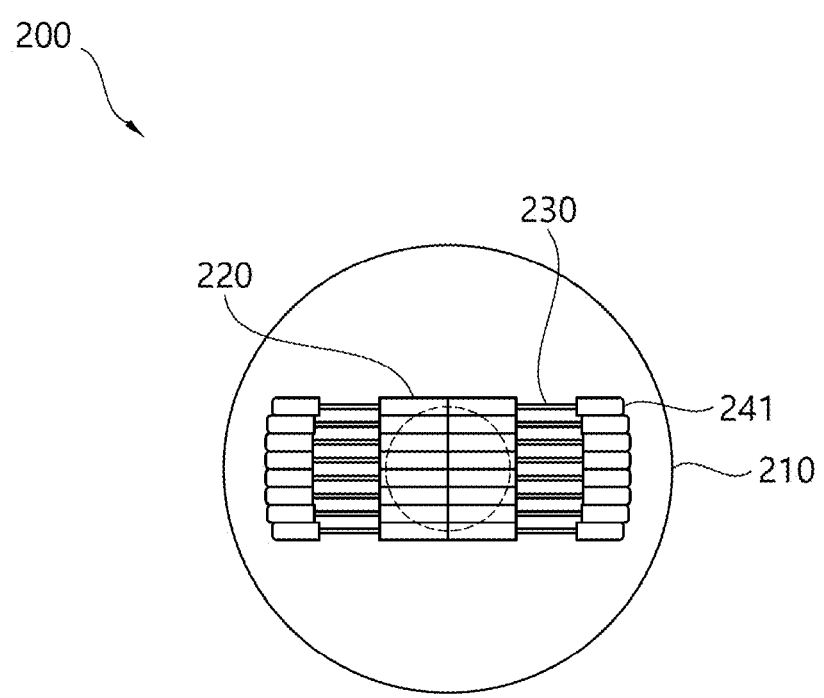
FIGS. 5A and 5B are enlarged plan views of a multi-leaf collimator module.
Figure 5B:
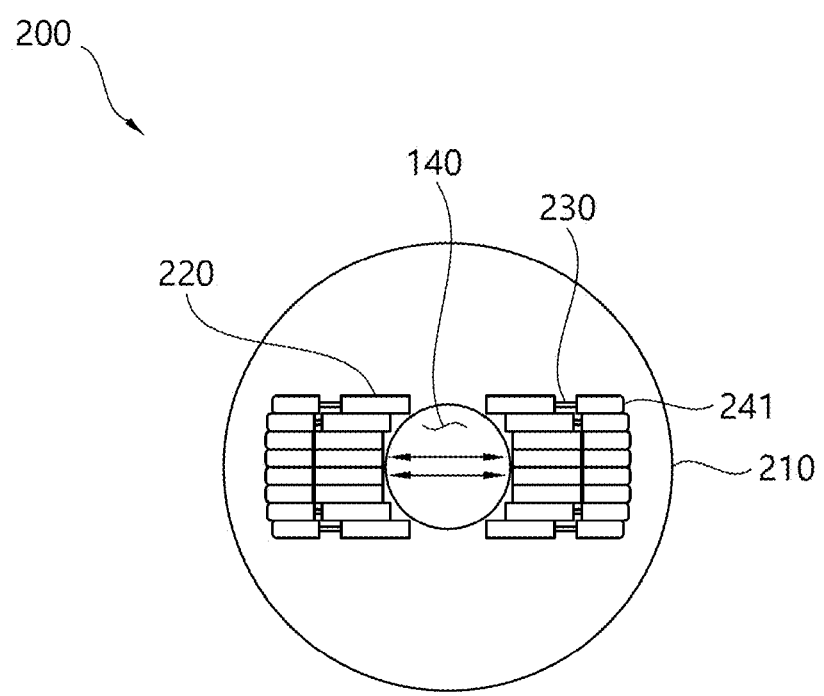

FIGS. 5A and 5B are enlarged plan views of the multi-leaf collimator module 200.

Referring to FIG. 5A, the multi-leaf collimator module 200 fully closes the center portion of the radiation irradiation area. As shown therein, the plurality of single-leaves 220 are dedicated to selectively close divisional portions of the radiation irradiation area.

Referring to FIG. 5B, the center portion of the radiation irradiation area is partially opened. As shown therein, the left four single-leaves 220 and the right four single-leaves 220 are moved to their opened positions, thereby forming an opened area only in the center portion.

Below, the operations of the dose adjustment system will be described in detail with reference to FIGS. 6A to 8B.

FIGS. 6A to 7B illustrate use of the dose adjustment system according to a second embodiment of the disclosure.

As shown therein, the dose adjustment system according to the second embodiment of the disclosure may include the dose adjustment device 1000 mountable to the diagnostic radiation apparatus 10, and a control device 600.

The control device 600 may be configured to receive an adjustment amount for the dose adjustment device 1000 from a user, and generate an adjustment signal for adjusting the dose adjustment device 1000. The control device 600 may include a display 610, the touch panel and the communication module 400. The control device 600 is configured to receive and display a diagnostic image obtained by a diagnostic radiation irradiation apparatus. Further, the control device 600 is configured to display the adjustment amount for the dose adjustment device 1000 together with the diagnostic image.

The control device 600 is configured to display a boundary line L between the opened area and the shielded area caused by the multi-leaf collimator module 200 on the display 610. For example, the boundary line L may be provided as a line connecting the centers on the sides of the single-leaves 220 facing the symmetric axis. The diagnostic image displayed on the display 610 is obtained in an actually shielded state, and it is thus possible to obtain an image of the shielded portions with the naked eyes. Further, the boundary line L displayed between the shielded area and the opened area makes it easier to recognize the images.

Figure 6A:
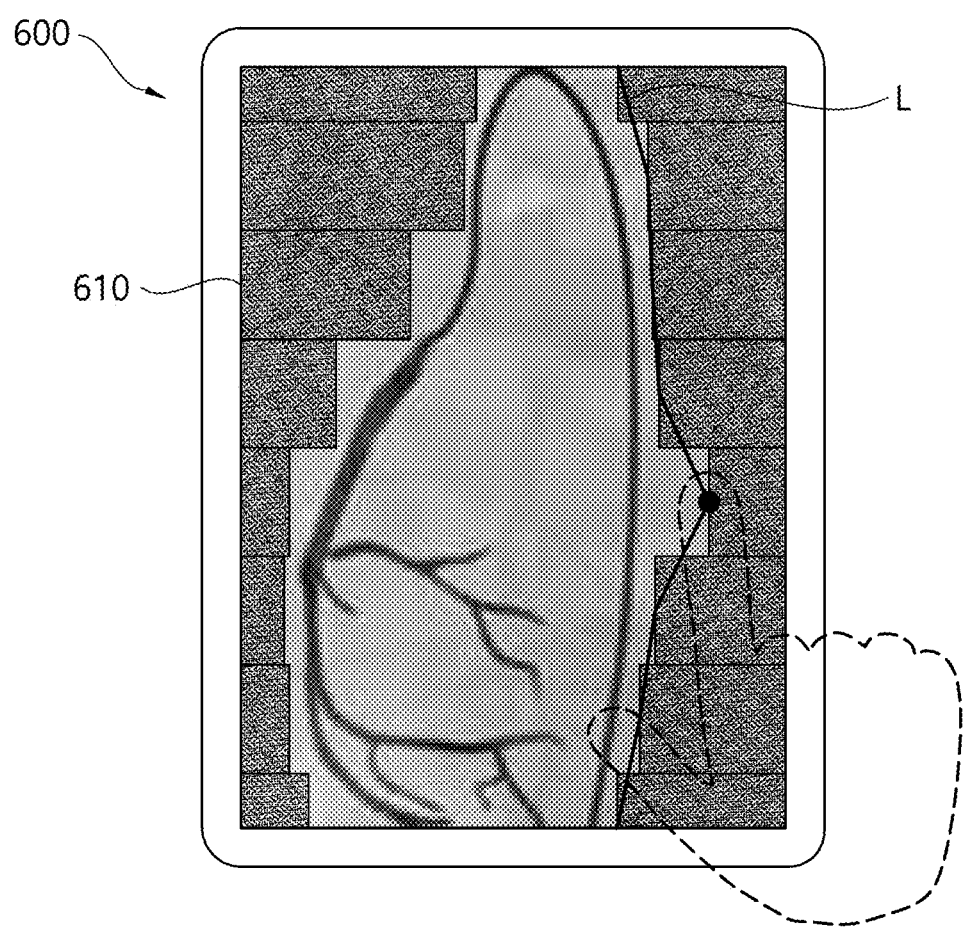
FIGS. 6A and 6B illustrate use of a dose adjustment system according to a second embodiment of the disclosure.
Figure 6B:
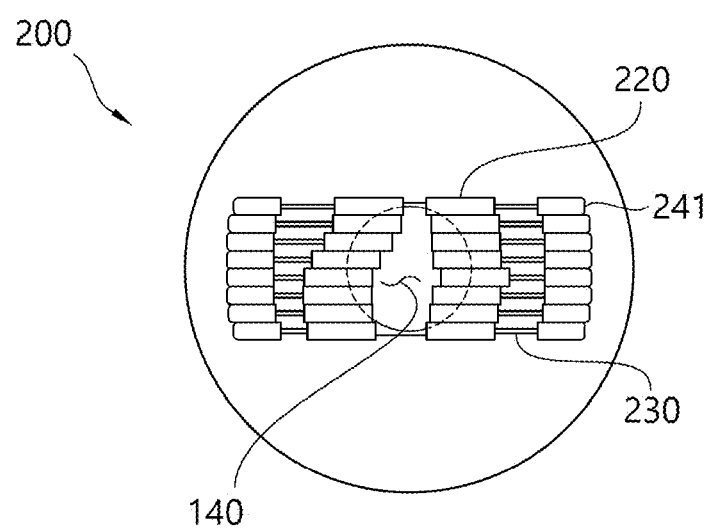

FIG. 6A shows a diagnostic image obtained corresponding to an affected area, and FIG. 6B shows a position combination of the multi-leaf collimator in the dose adjustment device 1000 corresponding to FIG. 6A. As shown therein, a shading difference between the shielded area and the opened area is made with respect to the boundary line L, and an area except a portion of which an image is needed to be obtained, for example, a portion including blood vessels is shielded from the radiation.

Figure 7A:
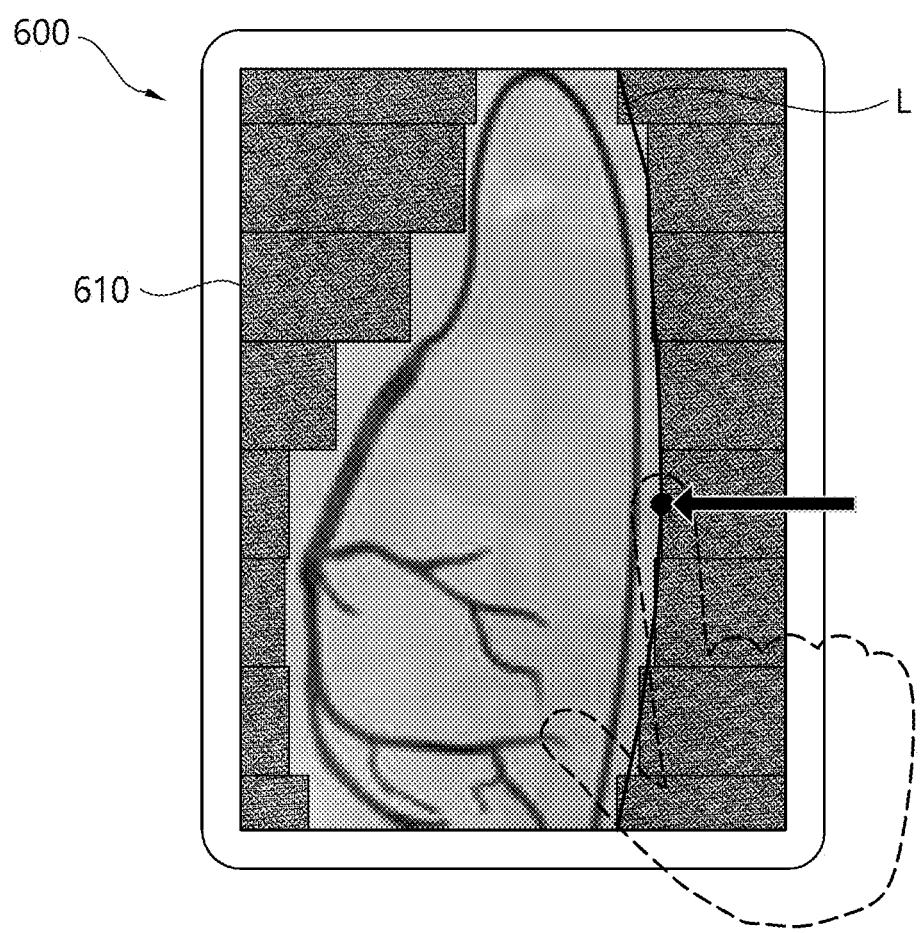
FIGS. 7A and 7B illustrate use of the dose adjustment system according to the second embodiment of the disclosure.
Figure 7B:
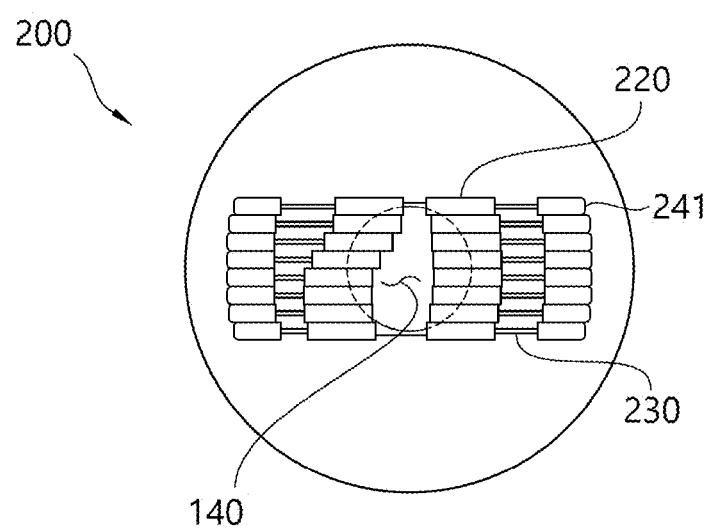

Referring to FIG. 7A, a user can touch and drag the screen of the control device 600 to move the boundary line L. The control device 600 receives an input for controlling the boundary line L and communicates with the dose adjustment device 1000, thereby selecting the single-leaves 220 to be adjusted, setting a moving amount of the selected single-leaves 220, and controlling the actuation unit 241. Referring to FIG. 7B, the shielded area is adjusted by a user's input shown in FIG. 7A in real time when the diagnostic image is obtained using the radiation.

Figure 8A:
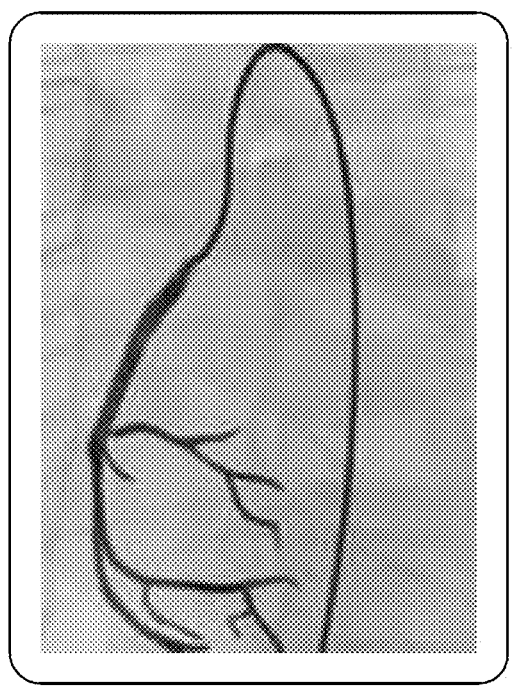
FIGS. 8A and 8B show images for comparison between before and after using a dose adjustment device according to another embodiment of the disclosure.
Figure 8B:
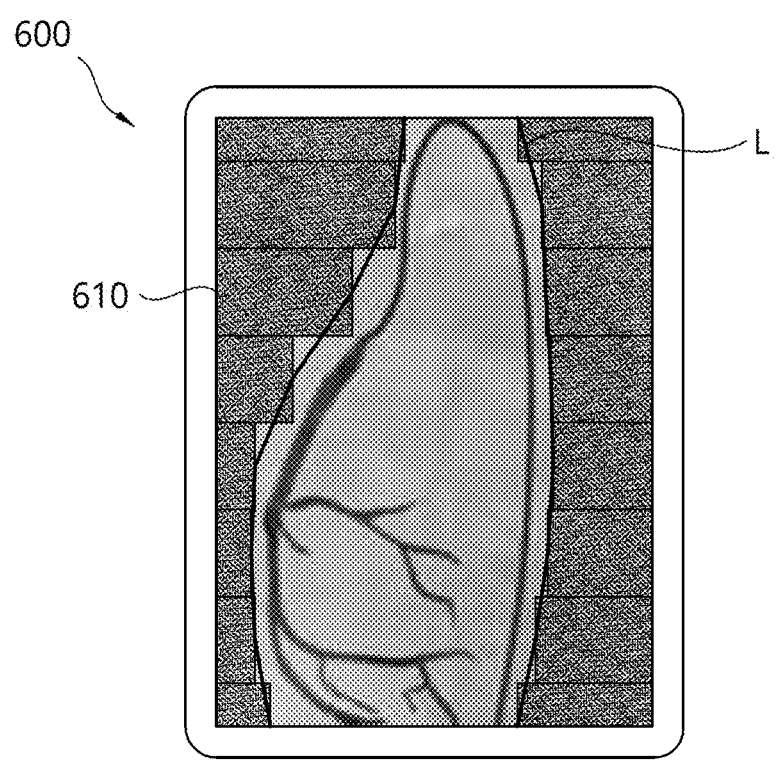

FIGS. 8A and 8B show images for comparison between before and after using the dose adjustment device 1000 according to another embodiment of the disclosure. FIG. 8A shows a conventional method. Referring to FIG. 8B, the radiation shielding rate of the multi-leaf collimator module 200 is not 100% unlike that of the conventional method. Therefore, a certain amount of radiation may pass through the multi-leaf collimator even though the radiation irradiation area is shielded by the multi-leaf collimator module 200. Eventually, it is possible to obtain a translucent image, which is visible to the naked eyes, in a radiation diagnostic image. According to this embodiment, when a user needs to check a rough image of an area outside the area of interest, the material or thickness of the single-leaf 220 may be provided to pass a certain amount of radiation. Specifically, the transmittance of an X-ray the multi-leaf collimator module 200 has may be within a range of 1% to 99%.

Figure 9A:
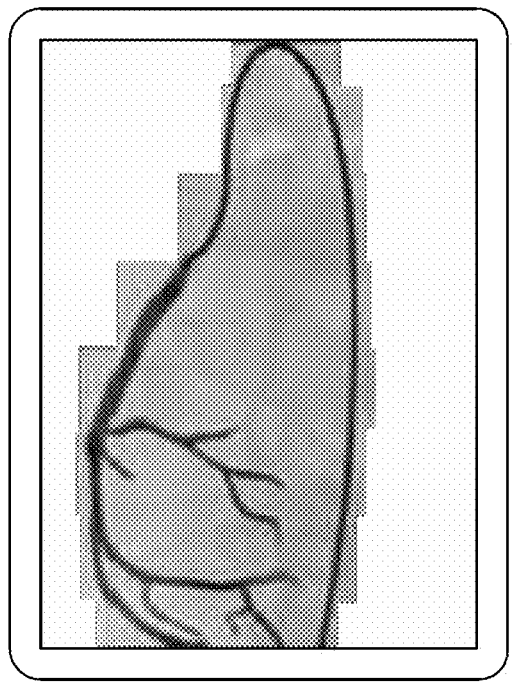
FIGS. 9A and 9B show images for comparison between before and after using a dose adjustment device according to still another embodiment of the disclosure.
Figure 9B:
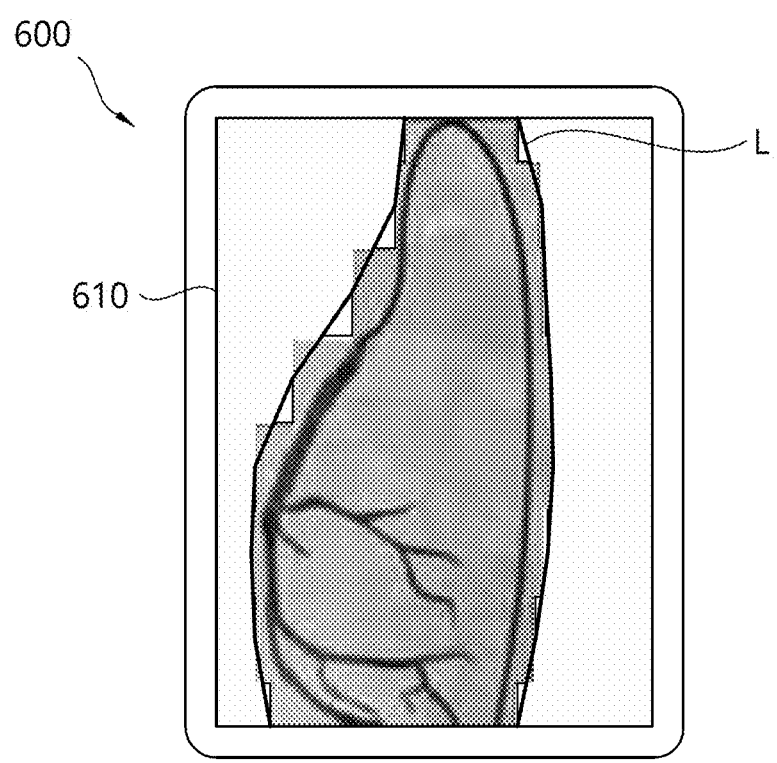

FIGS. 9A and 9B show images for comparison between before and after using the dose adjustment device according to still another embodiment of the disclosure. As shown therein, this embodiment shows an example that the multi-leaf collimator module 200 fully shields the diagnostic radiation. FIG. 9A shows that the multi-leaf collimator is not used in a conventional art. Referring to FIG. 9B, when the multi-leaf collimator is used according to the disclosure, an image of only an area opened through the multi-leaf collimator is obtained in an obtained diagnostic image, and a shielded area selected by a user is set and shielded from the radiation. According to this embodiment, the exposure to the radiation is fundamentally prevented in an area outside the area of interest.

Below, it will be described with reference to FIG. 10 that the disclosure is applied to a stationary diagnostic radiation apparatus 10.

Figure 10:
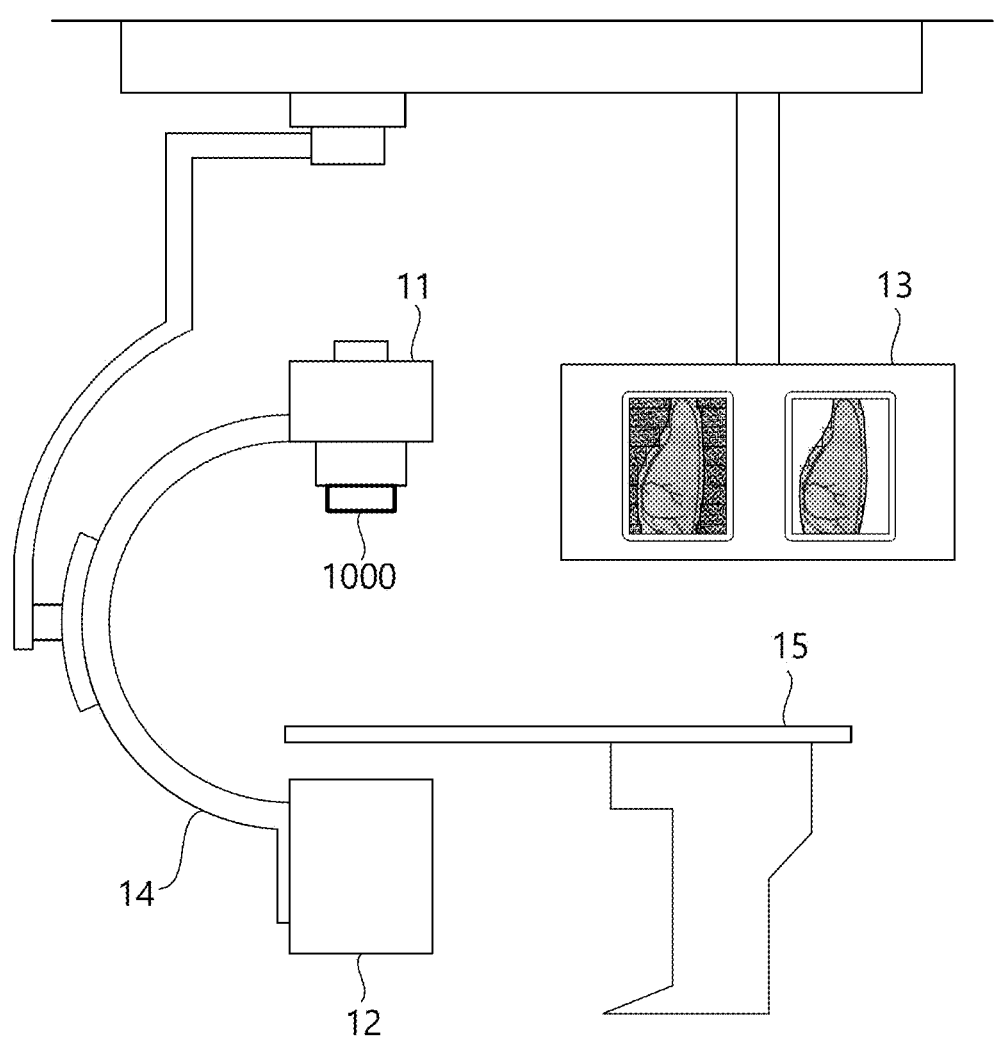
FIG. 10 is a conceptual view illustrating a stationary diagnostic radiation apparatus with a dose adjustment system according to the disclosure.

FIG. 10 is a conceptual view illustrating the stationary diagnostic radiation apparatus 10 with a dose adjustment system according to the disclosure.

As shown therein, as one among various types of the diagnostic radiation apparatus 10, the stationary diagnostic radiation apparatus 10 includes a C-arm 14 hanging from the ceiling and guided by a plurality of linear guides to move on a plane in a diagnosis room. The C-arm 14 is provided to move on the plane and obtain a radiation diagnostic image of a patient lying on a patient supporter 15. The display 610 and a control panel 13 may be connected to the ceiling and disposed so that a user can use the diagnostic radiation apparatus 10.

In the dose adjustment system according to the disclosure, the dose adjustment device 1000 may be mounted to the end portion of the radiation irradiator 11 of the C-arm 14 like that of the foregoing embodiment. Meanwhile, the diagnostic radiation apparatus 10 may be used instead of the control device 600. In this case, the dose adjustment device 1000 may be controlled through the control panel 13 of the diagnostic radiation apparatus 10 without separately using the control device 600.

As described above, the dose adjustment device according to the disclosure and the dose adjustment system including the same can adjust the shielding rate for each portion based on a user's input in real time when a diagnostic image is obtained. Further, the dose adjustment device provided as a single body is mounted to the diagnostic radiation apparatus and adjusts the dose, thereby having an effect on adding a function without changing the design of a conventional diagnostic radiation apparatus.

The invention claimed is:

1. A dose adjustment device mountable to a diagnostic radiation apparatus, the dose adjustment device comprising:
   a housing;
   a power supply comprising battery;
   a multi-leaf collimator configured to adjust transmittance for a portion in an irradiation area of diagnostic radiation;
   an actuator configured to individually adjust positions of single-leaves included in the multi-leaf collimator;
   a communication module configured to communicate with an outside; and
   a controller configured to control the actuator so that the transmittance for each portion in the irradiation area of the diagnostic radiation can be adjusted based on a signal received from the communication module,
   wherein the controller operates the actuator using the battery integrated into the dose adjustment device.

2. The dose adjustment device according to claim 1, wherein the dose adjustment device is provided between a radiation irradiator and a radiation detector of the diagnostic radiation apparatus.

3. The dose adjustment device according to claim 2, further comprising a connector detachably provided at an end portion of the radiation irradiator of the diagnostic radiation apparatus.

4. The dose adjustment device according to claim 3, wherein the single-leaves each extend on a plane perpendicular to an irradiating direction of the radiation, and are provided side by side being in close contact with each other.

5. The dose adjustment device according to claim 4, wherein the actuator comprises a plurality of actuation units to move each single-leaf in a direction where the single-leaf extends.

6. The dose adjustment device according to claim 5, wherein the housing is configured in a cylindrical housing accommodating the power supply, the multi-leaf collimator, the communication module, and the controller, and formed with a hollow in a center portion thereof through which the diagnostic radiation can pass.

7. The dose adjustment device according to claim 6, wherein
   the multi-leaf collimator is configured in two rows on the plane, and
   each row is configured to adjust the transmittance of a half area in the hollow.

8. The dose adjustment device according to claim 7, wherein the multi-leaf collimator, the power supply, the communication module and the controller are stacked as a plurality of layers inside the housing.

9. The dose adjustment device according to claim 1, wherein the radiation comprises an X-ray.

10. The dose adjustment device according to claim 9, wherein the single-leaf is configured to shield the X-ray.

11. The dose adjustment device according to claim 9, wherein the single-leaf is configured to transmit 1% to 99% of the X-ray.

12. A dose adjustment system mountable to a diagnostic radiation apparatus, the system comprising:
   a dose adjustment device detachably provided in the diagnostic radiation apparatus; and
   a control device configured to communicate with the dose adjustment device and receive an input of an adjustment amount for transmittance of radiation for a portion, the dose adjustment device comprising:

a housing:

a power supply comprising battery;

a multi-leaf collimator configured to adjust transmittance for a portion in an irradiation area of diagnostic radiation;

an actuator configured to individually adjust positions of single-leaves included in the multi-leaf collimator;

a communication module configured to communicate with the control device; and a controller configured to control the actuator so that the transmittance for each portion in the irradiation area of the diagnostic radiation can be adjusted based on a signal received from the communication module, wherein the controller operates the actuator using the battery integrated into the dose adjustment device.

13. The dose adjustment system according to claim 12, wherein the control device comprises a display, and is configured to receive an obtained diagnostic image from an external diagnostic radiation apparatus and display the received diagnostic image on the display.

14. The dose adjustment system according to claim 13, wherein the control device is configured to generate an adjustment signal for adjusting the multi-leaf collimator based on a touched position and a dragged amount when a user touches and drags an image on the display, and the controller controls the actuator based on the adjustment signal.

* * * * *